United States Patent
Nakagawa et al.

(10) Patent No.: US 8,598,188 B2
(45) Date of Patent: Dec. 3, 2013

(54) METHOD FOR PREDICTING THERAPEUTIC EFFICACY OF CHEMOTHERAPY ON NON-SMALL-CELL LUNG CANCER

(75) Inventors: Kazuhiko Nakagawa, Higashiosaka (JP); Isamu Okamoto, Higashiosaka (JP)

(73) Assignees: Kinki University, Osaka (JP); Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/255,550

(22) PCT Filed: Mar. 8, 2010

(86) PCT No.: PCT/JP2010/053795
§ 371 (c)(1), (2), (4) Date: Nov. 21, 2011

(87) PCT Pub. No.: WO2010/104035
PCT Pub. Date: Sep. 16, 2010

(65) Prior Publication Data
US 2012/0083503 A1 Apr. 5, 2012

(30) Foreign Application Priority Data
Mar. 12, 2009 (JP) .................................. 2009-059392

(51) Int. Cl.
*A61K 31/282* (2006.01)
*A61K 45/06* (2006.01)

(52) U.S. Cl.
USPC ............................. 514/274; 514/19.3; 435/7.4

(58) Field of Classification Search
USPC .................................. 514/274, 19.3; 435/7.4
See application file for complete search history.

(56) References Cited

FOREIGN PATENT DOCUMENTS

JP 2008-268167 6/2008

OTHER PUBLICATIONS

Gimaracil basic information document (Chemical book, 2008, downloaded from the internet on Feb. 26, 2013, URL: http://www.chemicalbook.com/ProductChyemicalPropertiesCB2362004.*
Oteracil chemical information document. (Chemical book, 2008, downloaded from the internet on Feb. 26, 2013, URL: http://www.chemicalbook.com/ProductChyemicalPropertiesCB9435346).*
Nakagawa et al. (Lung Cancer (2004), 43, pp. 145-149).*
Sanborn ( Current Treatment Options in Oncology, 2008, vol. 9, pp. 326-342).*
Kawahara et al. (British journal of Cancer (2001), vol. 85 (7), pp. 939-943).*
Kaira et al., "A phase I dose-escalation study of S-1 plus carboplatin in patients with advanced non-small-cell lung cancer", Anti-Cancer Drugs, 2007, 18: 471-476.
Lynch, "Lung Cancer Highlights", The Oncologist, 2000, 5: 274-279.
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan", Annals of Oncology, 18: 2007, 317-323.
Masayuki Takeda et al., Thymidylate synthase and dihydropyrimidine dehydrogenase expression levels are associated with response to S-1 plus carboplatin in advanced non-small cell lung cancer, Lung Cancer, vol. 73, No. 1, pp. 103-109, Oct. 28, 2010.
I. Okamoto et al., Phase III Trial Comparing Oral S-1 Plus Cabopatin With Paclitaxel Plus Carboplatin in Chemotherapy-Naive Patients With Adcanced Non-Small-Cell Lung Cancer: Results of a West Japan Oncology Group Study, Journal of Clinical Oncology, vol. 28, No. 36, pp. 5240-5246, Nov. 15, 2010.
Zhong Zheng et al, Thymidylate synthase in situ protein expression and survival in stage I nonsmall-cell lung cancer, Cancer, vol. 112, No. 12, pp. 2765-2773, Jun. 15, 2008.

* cited by examiner

*Primary Examiner* — Savitha Rao
(74) *Attorney, Agent, or Firm* — Rothwell, Figg, Ernst & Manbeck, P.C.

(57) ABSTRACT

This invention relates to an antitumor agent comprising carboplatin and a combination drug of tegafur/gimeracil/oteracil potassium to be administered to a cancer patient selected according to an expression level of thymidylate synthase gene.

5 Claims, No Drawings

METHOD FOR PREDICTING THERAPEUTIC EFFICACY OF CHEMOTHERAPY ON NON-SMALL-CELL LUNG CANCER

TECHNICAL FIELD

The present invention relates to a method for predicting a therapeutic effect of combination chemotherapy with carboplatin and a combination drug of tegafur/gimeracil/oteracil potassium; and an antitumor agent to be administered to a patient who is likely to sufficiently respond to the combination chemotherapy. The present invention also relates to a therapeutic method of non-small-cell lung cancer, and a use of an antitumor agent comprising carboplatin and a combination drug of tegafur/gimeracil/oteracil potassium.

BACKGROUND ART

Currently, a combination of cisplatin and the third-generation antitumor agents (paclitaxel, docetaxel, gemcitabine, vinorelbine or irinotecan), or a combination of carboplatin and paclitaxel is used for standard treatment of advanced non-small-cell lung cancers (Non-patent Documents 1 and 2). However, since these standard treatments merely ensure a response rate of 15.3 to 33.0% and a progression-free survival of four months, the therapeutic effect is not satisfactory.

In addition to those standard treatments, research has been conducted to find combination chemotherapy for non-small-cell lung cancers that can ensure a greater therapeutic effect. For example, a clinical test for a combined use of TS-1 (a combination drug of tegafur/gimeracil/oteracil potassium (mole ratio=1:0.4:1)) and carboplatin was reported. However, the test showed that the response rate of the combined use of these drugs was 33.0%, which is substantially the same as that of the standard treatments (Non-patent Document 3).

As described above, although various combination chemotherapies for treating advanced non-small-cell lung cancer have been intensively developed, the therapeutic efficacies of these treatments are not satisfactory. Therefore, a chemotherapy that ensures further significant therapeutic effects is required.

CITATION LIST

Patent Document
Non-patent Document 1: Oncologist. 2000; 5(4):274-9.
Non-patent Document 2: Ann Oncol. 2007; 18(2):317-23.
Non-patent Document 3: Anticancer Drugs. 2007; 18(4): 471-6.

SUMMARY OF INVENTION

Technical Problem

An object of the present invention is to provide an antitumor agent for non-small-cell lung cancer that ensures a significant therapeutic effect; and a method for predicting therapeutic effect of combination chemotherapy using carboplatin and a combination drug of tegafur/gimeracil/oteracil potassium, to a non-small-cell lung cancer patient who is not sufficiently responding to known therapeutic methods. Another object of the present invention is to provide a therapeutic method for non-small-cell lung cancer, and a use of an antitumor agent comprising carboplatin and a combination drug of tegafur/gimeracil/oteracil potassium.

Solution to Problem

The inventors of the present invention conducted extensive research to enhance the therapeutic effect (tumor-shrinking effect, effect of prolonging progression-free survival or life-prolonging effect, etc.) of combination chemotherapy for treating non-small-cell lung cancer, and found that a combination therapeutic method using carboplatin and a combination drug of tegafur/gimeracil/oteracil potassium ensures a more significant therapeutic effect than the existing methods with respect to patients selected according to the expression level of thymidylate synthase gene. Based on this finding, the inventors completed the present invention.

More specifically, the present invention provides a method for predicting therapeutic effect of combination chemotherapy with carboplatin and a combination drug of tegafur/gimeracil/oteracil potassium with respect to non-small-cell lung cancer patients; an antitumor agent comprising carboplatin and a combination drug of tegafur/gimeracil/oteracil potassium; a therapeutic method of non-small-cell lung cancers; and a use of an antitumor agent comprising carboplatin and a combination drug of tegafur/gimeracil/oteracil potassium.

Item 1. A method for predicting a therapeutic effect of combination chemotherapy with carboplatin and a combination drug of tegafur/gimeracil/oteracil potassium with respect to non-small-cell lung cancer patients,
the method comprising the steps of:
(1) measuring an expression level of thymidylate synthase gene in a biological sample, which is obtained from a patient and is likely to contain cancer cells; and
(2) predicting that the patient is likely to sufficiently respond to the combination chemotherapy when the expression level measured in Step (1) is lower than a predetermined cut-off point.

Item 2. The method according to Item 1, wherein the molar ratio of tegafur, gimeracil, and oteracil potassium is 1:0.4:1.

Item 3. An antitumor agent comprising carboplatin and a combination drug of tegafur/gimeracil/oteracil potassium, characterized by performing the combination chemotherapy with respect to a cancer patient assumed to sufficiently respond to the combination chemotherapy in accordance with a result of the method of Item 1 or 2.

Item 4. A therapeutic method of non-small-cell lung cancer, characterized by performing the combination chemotherapy with respect to a cancer patient assumed to sufficiently respond to the combination chemotherapy in accordance with a result of the method of Item 1 or 2.

Item 5. Use of an antitumor agent comprising carboplatin and a combination drug of tegafur/gimeracil/oteracil potassium to perform the combination chemotherapy with respect to a cancer patient assumed to sufficiently respond to the combination chemotherapy in accordance with a result of the method of Item 1 or 2.

Advantageous Effects of Invention

The therapeutic method of the present invention using carboplatin and a combination drug of tegafur/gimeracil/oteracil potassium is expected to ensure a significantly greater therapeutic effect (tumor-shrinking effect, effect of prolonging progression-free survival or life-prolonging effect, etc.) than the existing methods with respect to non-small-cell lung cancer patients selected according to the index, i.e., the expression level of thymidylate synthase gene.

DESCRIPTION OF EMBODIMENTS

The prediction method of the present invention predicts those patients who are likely to more strongly respond to combination chemotherapy with carboplatin and a combination drug of tegafur/gimeracil/oteracil potassium based on the expression level of thymidylate synthase gene in patients.

In the present invention, "combination chemotherapy with carboplatin and a combination drug of tegafur/gimeracil/oteracil potassium" means chemotherapy in which both antitumor agents, i.e., carboplatin and a combination drug of tegafur/gimeracil/oteracil potassium, are administered in combination. When carboplatin and the combination drug are administered in combination, they may be administered simultaneously, or separately at a fixed interval.

In the present invention, "sufficiently respond to the combination chemotherapy" indicates a condition in which the patient responds to the combination chemotherapy to a greater extent (in terms of tumor-shrinking effect, effect of prolonging progression-free survival or life-prolongation effect, etc.) than that achieved with standard therapies (for example, cisplatin/vinorelbine or carboplatin/paclitaxel combination chemotherapy). Whether such a condition is shown can be determined by finding out whether the expression level of thymidylate synthase gene is equal to or less than a cut-off point. The expression level of thymidylate synthase gene that is equal to or less than a cut-off point is regarded as ensuring a sufficient therapeutic effect of the combination chemotherapy.

Tegafur (generic name, chemical name: 5-fluoro-1-(2-tetrahydrofuryl)-2,4-(1H,3H)-pyrimidinedione), an active ingredient in the present invention, is a known compound, and is a drug that is activated in vivo to release 5-fluorouracil, which is a substance responsible for the antitumor activity. Tegafur can be produced according to known methods, for example, the method disclosed in Japanese Examined Patent Publication No. S49-10510.

Gimeracil (generic name, chemical name: 2,4-dihydroxy-5-chloropyridine), an active ingredient in the present invention, is also a known compound. Although gimeracil itself does not exhibit any antitumor activity, it can inhibit metabolic inactivation of 5-fluorouracil in vivo, thereby potentiating the antitumor effect.

Oteracil potassium (generic name, chemical name: monopotassium 1,2,3,4-tetrahydro-2,4-dioxo-1,3,5-triazine-6-carboxylate), an active ingredient in the present invention, is also a known compound. Although oteracil potassium itself does not exhibit any antitumor activity, it is chiefly distributed in the gastrointestinal tract, where it inhibits the activation of 5-fluorouracil, thereby preventing gastrointestinal tract disorders.

Carboplatin (generic name, chemical name: cis-diammine (1,1-cyclobutanedicarboxylato)platinum(II)), an active ingredient in the present invention, is a known platinum complex compound, and is known to exhibit an antitumor effect due to DNA synthesis inhibitory action. Carboplatin can be produced according to known methods, for example, the method disclosed in Japanese Examined Patent Publication No. S56-029676. Further, commercially available pharmaceutical products, such as Paraplatin (registered trademark, produced by Bristol-Myers Co.), may be used.

The therapeutic effect in the present invention can be evaluated comprehensively by a tumor-shrinking effect, effect of prolonging progression-free survival or life-prolongation effect, etc., each of which can be determined by the degree of tumor shrinkage, overall survival, progression-free survival, etc. Progression-free survival can be indicated by median progression-free survival (the longer the survival, the greater the therapeutic effect). Overall survival can be indicated by median overall survival (the longer the survival, the greater the therapeutic effect).

The proportion of tegafur, gimeracil and oteracil potassium that are administered in the present invention is not particularly limited as long as the purpose of each ingredient is achieved. For example, the proportion of tegafur, gimeracil and oteracil potassium may be within the same range as that in the known combination preparation disclosed in Patent Publication No. 2614164. It is usually such that, per mole of tegafur, gimeracil is used in a proportion of about 0.1 to about 5 moles and preferably about 0.2 to about 1.5 moles, and oteracil potassium is used in a proportion of about 0.1 to about 5 moles and preferably about 0.2 to about 2 moles. It is particularly preferred that the molar ratio of tegafur:gimeracil:oteracil potassium is 1:0.4:1.

The proportion of carboplatin that is administered in the present invention is not particularly limited as long as an antitumor effect is attained. For example, it is usually such that, per mole of tegafur, carboplatin is used in a proportion of about 0.1 to about 5.0 moles, preferably about 0.3 to about 3.0 moles, and more preferably about 1.0 to about 2.5 moles as a daily dose.

The dose of each active ingredient in the present invention can be suitably selected according to conditions such as dose regimen, age and sex of a patient, stage of disease, presence or absence of metastasis, medical history, and presence or absence of other antitumor agents. The pharmaceutical preparations of the present invention are preferably given in an amount using the following range as a standard: the amount of tegafur is about 0.1 to about 100 mg/kg/day, preferably about 0.2 to about 40 mg/kg/day, and more preferably about 0.5 to about 20 mg/kg/day; the amount of gimeracil is about 0.02 to about 30 mg/kg/day, preferably about 0.05 to about 12 mg/kg/day, and more preferably about 0.1 to about 6 mg/kg/day; the amount of oteracil potassium is about 0.1 to about 100 mg/kg/day, preferably about 0.2 to about 40 mg/kg/day, and more preferably about 0.5 to about 20 mg/kg/day; and the amount of carboplatin is about 0.08 to about 200 mg/kg/day, preferably about 0.15 to about 80 mg/kg/day, and more preferably about 0.4 to about 40 mg/kg/day. Further, each active ingredient is administered in a single dose or multiple divided doses per day. Active ingredients are administered simultaneously or separately at intervals, and the order of administration thereof is not particularly limited.

In the present invention, tegafur, gimeracil, and oteracil potassium are provided as a combination preparation that is formulated into one dosage form. Furthermore, in the present invention, carboplatin may be formulated alone to form a single active ingredient preparation, or formulated in combination with tegafur, gimeracil, and oteracil potassium into one dosage form to form a combination preparation. Preferably, carboplatin is formulated alone into one dosage form to form a single active ingredient preparation.

As long as active ingredients are administered in combination, each of the above preparations may be individually produced, packed, and distributed, or all or a part of the preparations may be produced, packed, and distributed as a single package (kit formulation) suitable for administering in combination.

The dosage form of the preparations of the present invention is not particularly limited, and specific examples thereof include oral preparations (such as tablets, coated tablets, powders, granules, capsules, and fluids), injections, suppositories, patches, and ointments. When the active ingredients of the present invention are formulated into a plurality of dosage forms, the preparations may be presented in different dosage forms, or in the same dosage form. For example, the combination drug of tegafur/gimeracil/oteracil potassium is preferably an oral preparation, and the preparation containing carboplatin is preferably an injection.

The preparations of the present invention are produced using a pharmacologically acceptable carrier by formulation methods that are commonly known in each dosage form. Examples of the carrier include those that are widely used in common drugs, such as excipients, binders, disintegrators, lubricants, diluents, solubilizing agents, suspending agents, tonicity adjusting agents, pH adjusters, buffers, stabilizers, colorants, sweetening agents, flavoring agents, and soothing agents.

Examples of excipients include lactose, saccharose, sodium chloride, glucose, maltose, mannitol, erythritol, xylitol, maltitol, inositol, dextran, sorbitol, albumin, urea, starch, calcium carbonate, kaolin, crystalline cellulose, silicic acid, methylcellulose, glycerol, sodium alginate, gum arabic, and mixtures thereof. Examples of lubricants include purified talc, stearic acid salts, borax, polyethylene glycol, and mixtures thereof. Examples of binders include simple syrups, glucose solutions, starch solutions, gelatin solutions, polyvinyl alcohol, polyvinyl ether, polyvinylpyrrolidone, carboxymethylcellulose, shellac, methylcellulose, ethylcellulose, water, ethanol, potassium phosphate, and mixtures thereof. Examples of disintegrators include dried starch, sodium alginate, powdered agar, powdered laminaran, sodium hydrogencarbonate, calcium carbonate, polyoxyethylene sorbitan fatty acid esters, sodium lauryl sulfate, stearic acid monoglycerides, starch, lactose, and mixtures thereof. Examples of diluents include water, ethyl alcohol, macrogol, propylene glycol, ethoxylated isostearyl alcohol, polyoxylated isostearyl alcohol, polyoxyethylene sorbitan fatty acid esters, and mixtures thereof. Examples of stabilizers include sodium pyrosulfite, ethylene diamine tetraacetic acid, thioglycolic acid, thiolactic acid, and mixtures thereof. Examples of tonicity adjusting agents include sodium chloride, boric acid, glucose, glycerol, and mixtures thereof. Examples of pH-adjusters and buffers include sodium citrate, citric acid, sodium acetate, sodium phosphate, and mixtures thereof. Examples of soothing agents include procaine hydrochloride, lidocaine hydrochloride and mixtures thereof. Examples of solubilizing agents include polyethylene glycol, and D-mannitol. Examples of suspending agents include stearyltriethanolamine, sodium lauryl sulfate, and benzalkonium chloride. Examples of colorants include titanium oxide and iron oxide. Examples of sweetening/flavoring agents include saccharose, orange peel, citric acid, and tartaric acid.

The administration schedule in the present invention can be suitably selected according to conditions such as the age and sex of a patient, stage of disease, presence or absence of metastasis, and medical history. For example, the combination chemotherapy of the present invention is preferably conducted according to the following schedule. During a three-week period, tegafur, gimeracil and oteracil potassium are administered for 14 consecutive days followed by a 7-day withdrawal, and on the first day of the consecutive administration, carboplatin is administered. This is regarded as one cycle, and one cycle or a plurality of cycles are conducted.

The target patients for the prediction method of the present invention are patients with non-small-cell lung cancer, and may also be patients with non-small-cell lung cancer as a primary focus and with non-small-cell lung cancer that has metastasized to an organ or tissue other than the lung.

Biological samples that can be used in measuring the expression level of thymidylate synthase gene in the present invention are not particularly limited as long as they are likely to contain cancer cells. Examples thereof include body fluid (such as blood and urine), tissues, or the extracts thereof, and cultures of the obtained tissues. Methods for collecting biological samples can be suitably selected according to the type of biological samples or type of cancers. For example, tumor tissues of surgical or biopsy specimens that are obtained prior to chemotherapy can be mentioned. The preparation of DNA, RNA, and proteins from biological samples can be conducted according to commonly known methods. As the tissues, the lung can be mentioned in particular; however, when cancer cells have metastasized from the lung to other organs, peritoneum, or the like, the tissues at the metastasis sites become target tissues.

The expression level of thymidylate synthase gene can be measured by separating cancer cells from a sample that is likely to contain cancer cells, separating a protein or mRNA of thymidylate synthase from the cancer cells, and either immunologically measuring the thymidylate synthase protein, or amplifying the mRNA with amplification means, such as PCR, and detecting the resulting mRNA.

The expression level of mRNA of thymidylate synthase gene can be quantified as a ratio to a control, such as beta actin, according to TaqMan (registered trademark) real-time PCR method, for example, by extracting total RNA from formalin-fixed paraffin-embedded sections of tumor tissues of surgical or biopsy specimens obtained prior to chemotherapy.

Thymidylate synthase is an enzyme that has an activity of synthesizing dTMP from dUMP using folic acid as a coenzyme, and is known as an enzyme required in DNA synthesis. Further, thymidylate synthase is known as a target enzyme of 5-fluorouracil. The base sequence and amino acid sequence of human thymidylate synthase gene are known (Nucleic Acids Res. 13:2035-2043 (1985)).

The prediction method of the present invention employs the expression level of thymidylate synthase gene as an index. The expression level may be that of mRNA, or that of a protein. Here, the expression level of mRNA can be measured using a probe or primer that specifically hybridizes with thymidylate synthase gene, according to known methods for measuring gene expression levels, such as Northern blotting method, quantitative or semi-quantitative PCR method (for example, RT-PCR method and real-time PCR method), and in situ hybridization method. The above expression level can be assessed by comparison with a protein/gene that is expressed at a constant level (for example, a housekeeping gene, such as $\beta$-actin, or its expressed protein) as a reference standard.

The level of protein expression can be measured by conducting a known immunological assay, such as an enzyme immunoassay, radioimmunoassay, competitive immunoassay, double antibody sandwich assay, fluoroimmunoassay, ELISA, Western blotting technique, agglutination assay, cytofluorometry, or immunohistochemical staining assay, using an antibody that specifically recognizes thymidylate synthase. Preferred tissue specimens to perform an assay by immunohistochemical staining, for example, include cell smears, tissue sections from biopsied tissues or organs, and imprint preparations among other tissue samples. Such tissue specimens can be maintained in various manners: for example, they can be fresh, frozen, or formalin-, alcohol-, acetone- or otherwise fixed and/or paraffin-embedded and deparaffinized. Biopsied tissue samples can be, for example, those samples removed by aspiration, bite, brush, cone, chorionic villus, endoscope, excision, incision, needle, percutaneous puncture, and surface biopsies, among other biopsy methods. The level of thymidylate synthase protein expression may be assessed as compared to normal human tissues of patients or someone other than the patients. The methods for assessing the measurement results obtained by immunohistochemical staining assays include, for example, the H-score method. The H-score is determined by the following calculation formula (Am J Clin Pathol. 1988; 90 (3): 233-9).

H-score=ρ (staining intensity×percentage of positive cells (%))

(staining intensity 0: unstained,
staining intensity 1: weak staining,
staining intensity 2: moderate staining,
staining intensity 3: strong staining)

It has been revealed that the H-score can be a value of 0 to 300, and that when the H-score is lower than a cut-off point, sufficient prolongation of progression-free survival is observed in chemotherapy that uses the antitumor agents of the present invention.

In assessment by the H-score method, one of serial sections of formalin-fixed paraffin-embedded blocks is stained with hematoxylin and eosin (HE) in advance, a pathologist identifies the presence or absence of cancer cells and distinguishes cancer cells from normal cells, and only cancer cell portions are used for H-score assessment. For negative or positive controls for staining intensity, formalin-fixed paraffin-embedded cell lines (several types of lines whose protein expression levels are known in advance) may be employed. When there are no control specimens, a plurality of specimens are assessed simultaneously to confirm the overall distribution of staining intensity of the specimens, and then staining intensity may be set. Regarding assessed sites, it is desirable to assess the entire specimen; however, it is possible to assess only one representative field. As tissue samples, either tissues of primary foci or metastatic foci of non-small-cell lung cancer can be assessed.

In addition to the H-score method, other scoring methods, such as the Allred method (Allred DC et al. Mod Pathol 1998; 11:155-68), can also be used. Cut-off points are required to be set in each method.

Allred score=score of percentage of positive cells+staining intensity score (score of percentage of positive cells 0: unstained,
score of percentage of positive cells 1: less than 1%,
score of percentage of positive cells 2: 1% to less than 10%,
score of percentage of positive cells 3: 10% to less than ⅓,
score of percentage of positive cells 4: ⅓ to less than ⅔,
score of percentage of positive cells 5: ⅔ or more)
(staining intensity 0: unstained,
staining intensity 1: weak staining,
staining intensity 2: moderate staining,
staining intensity 3: strong staining)

Probes used in the methods for measuring gene expression levels, such as Northern blot technique and in situ hybridization, are designed, according to commonly known probe design methods, to specifically hybridize with a continuous base sequence of at least 15 bases to the total base length, preferably 20 bases to the total base length, more preferably 30 bases to the total base length, of the base sequence of thymidylate synthase gene; and are in the form of polynucleotides having the above-mentioned base length.

Primers and probes used in quantitative or semi-quantitative PCR method, such as RT-PCR method and real-time PCR method, are designed, for example, in the following manner.

The primers and probes of the present invention are designed according to commonly known primer and probe design methods, to specifically hybridize with a continuous base sequence of at least 10 bases to the total base length, preferably 10 to 100 bases, more preferably 10 to 50 bases, still more preferably 10 to 35 bases of the base sequence of thymidylate synthase gene; and are in the form of polynucleotides having the above-mentioned base length. For example, primers for detecting the expression products of thymidylate synthase gene, i.e., forward and reverse primers for PCR, can be designed and synthesized from exon regions of thymidylate synthase gene. The forward and reverse primers are designed such that one is designed based on the base sequence of the upstream region of exon regions of thymidylate synthase gene (forward primer), and the other is designed based on the base sequence of the downstream region of the exon regions (reverse primer). For example, in designing thymidylate synthase gene primers based on exons 1 to 3, when the forward primer is designed based on the sequence of the exon 1 region, the reverse primer is designed based on the sequence of the downstream exon 2 region or exon 3 region. The reverse primer is designed to be complementary to the sequence of mRNA of thymidylate synthase gene. Further, each primer can be made using the whole and a part of the base sequence of mRNA of thymidylate synthase gene containing the exon region; however, it is desirable to design each primer in consideration of the efficiency of amplification from the exon region in PCR.

Probes for detecting expression products of thymidylate synthase gene are not particularly limited as long as they can hybridize with a single-stranded DNA of thymidylate synthase gene, which is amplified using the above primers by a PCR reaction. Any probes may be used as long as they have a sequence complementary to the base sequence of all exons of thymidylate synthase gene or a portion thereof, or as long as they are hybridizable under a stringent condition.

The probes are not always required to be fully complementary to the base sequence of thymidylate synthase gene as long as they specifically hybridize with thymidylate synthase gene. Such polynucleotides have an identity of not less than 70%, preferably not less than 80%, more preferably not less than 90%, still more preferably not less than 95%, and still further more preferably not less than 98%, in the base sequence, as compared to either the polynucleotide having a continuous base sequence of preferably at least 15 bases of the base sequence of thymidylate synthase gene or the complementary polynucleotide thereof.

In the present invention, "specific hybridization" refers to a hybridization that forms a specific hybrid and does not form a nonspecific hybrid under a stringent hybridization condition. The stringent hybridization condition can be determined according to commonly known methods, for example, based on the melting temperature (Tm) of the nucleic acid at which the hybrid is formed. A specific cleaning condition to maintain the hybridization condition is commonly about "1×SSC, 0.1% SDS, 37° C.," more strictly "0.5×SSC, 0.1% SDS, 42° C.," and still more strictly "0.1×SSC, 0.1% SDS, 65° C."

Because the base sequence of thymidylate synthase gene in humans is known, the probes or primers can be made by commonly known synthesis methods, for example, using a commercially available nucleotide synthesizer, based on the base sequence. The probes or primers can also be prepared by PCR method using the base sequence as a template.

Moreover, to easily detect thymidylate synthase gene, the probes or primers may be labeled with a commonly used radioactive substance, fluorescent substance, chemical luminescent substance, or enzyme.

The antibody of the present invention for measuring the level of thymidylate synthase protein expression is not particularly limited as long as it specifically recognizes human thymidylate synthase. The antibody may be either monoclonal or polyclonal; or an antibody fragment, such as Fab and F(ab')2 fragments. This antibody can be produced according to commonly known methods (for example, Current Protocols in Molecular Biology, Edit. Ausubel et al. (1987), Publish. John Wiley and Sons. Section 11.12-11.13). Furthermore, known anti-thymidylate synthase antibodies can be used (Gan To Kagaku Ryoho. 1997; 24 (6): 705-12).

In the step of predicting whether combination chemotherapy with carboplatin and a combination drug of tegafur/gimeracil/oteracil potassium should be performed, it is predicted that when the expression level of thymidylate synthase gene is lower than a predetermined cut-off point, the patient is likely to sufficiently respond to the combination chemotherapy.

The cut-off point in the present invention varies depending on conditions, such as subjects to be measured and the type of measurement methods, and therefore is required to be set in advance according to the conditions. Because the cut-off point varies according to subjects to be measured (the number, age, sex, body weight, health state, disease state of patients), measurement methods (which expression product, either gene or protein, is used for measurement), measurement conditions (for example, sequences of primers and probes in measuring gene expression products (mRNA), the type of labeling, the type and sensitivity of an antibody in the case where the expression product is a protein, and the like), statistical techniques, or other conditions, the present invention widely encompasses inventions using an arbitrary cut-off point that can be varied depending on these conditions, and is not limited to a particular value. Here, the cut-off point can be determined from the previously measured expression level of thymidylate synthase gene by using various statistical analysis techniques. Examples thereof include the average or median value of the expression level of thymidylate synthase gene in patients who have undergone combination chemotherapy with carboplatin and a combination drug of tegafur/gimeracil/oteracil potassium; values determined based on ROC (Receiver Operating Characteristic) analysis such that the sum of sensitivity and specificity becomes maximal from the relevance between the expression level of thymidylate synthase gene in patients who have undergone combination chemotherapy with carboplatin and a combination drug of tegafur/gimeracil/oteracil potassium, and with or without a certain therapeutic effect (response rate, life-prolongation effect, etc.) of the combination chemotherapy; and values determined based on the chi-square test from the relevance between the expression level of thymidylate synthase gene in patients who have undergone combination chemotherapy with carboplatin and a combination drug of tegafur/gimeracil/oteracil potassium, and a therapeutic effect (response rate, life-prolongation effect, etc.) of the combination chemotherapy (among them, values in which the P-value of the log-rank test becomes minimal or below a certain level (for example, values determined such that the P-value is 0.1 or less, or 0.05 or less)).

As a result, for example, when only cancer cell portions taken from patients with non-small-cell lung cancer are measured based on immunohistochemical staining assays and calculated by the H-score method, the cut-off point for thymidylate synthase gene in this combination chemotherapy is preferably 30 to 70, more preferably 30 to 45, and still more preferably 45.

EXAMPLE

An Example is given below to illustrate the present invention in more detail; however, the scope of the present invention is not limited to the Example.

Example 1

In a clinical trial of TS-1/carboplatin combination therapy for chemotherapy-naive patients with stage IIIB/IV advanced non-small-cell lung cancer, a biomarker study (measurement of the protein expression level of thymidylate synthase) was conducted as an additional study.

A single dose of TS-1 was the following initial standard dose per body surface area. TS-1 was orally administered twice a day, after breakfast and after dinner. The initial standard dose was 40 mg/dose (80 mg/day) for less than 1.25 $m^2$ of body surface area; 50 mg/dose (100 mg/day) for 1.25 $m^2$ or more to less than 1.50 $m^2$ of body surface area; and 60 mg/dose (120 mg/day) for 1.50 $m^2$ or more of body surface area.

The dose of carboplatin was calculated so that an area under the blood concentration-time curve (hereinafter referred to as AUC) was 5 min·mg/mL, according to the Calvert formula below.

Calvert Formula

Carboplatin dose (mg/body)=AUC (min·mg/mL)× [creatinine clearance (mL/min)+25]

Cockcroft-Gault Method

Creatinine clearance (mL/min)=[(140-age)×body weight (kg)]/serum creatinine (mg/dL)×72)

For females, the calculated creatinine clearance was multiplied by 0.85.

TS-1 was orally administered for 14 consecutive days, followed by a 7-day withdrawal.

On the first day of 14 consecutive days of TS-1 administration, carboplatin was mixed with 250 mL of physiological saline or 5% glucose solution, and the mixture was administered by one-hour intravenous injection.

The above 21 days were regarded as one course, and administration was conducted for 3 or more courses, up to 6 courses.

As a control, paclitaxel/carboplatin combination therapy was conducted.

The dose of paclitaxel was 200 mg/$m^2$ based on body surface area.

The dose of carboplatin was AUC 6 min·mg/mL according to the above Calvert formula. For females, the calculated creatinine clearance was multiplied by 0.85.

One course consisted of 21 days. On the first day, 200 mg/$m^2$ of paclitaxel was mixed with 500 mL of physiological saline or 5% glucose solution, and the mixture was administered by 3-hour intravenous drip infusion; immediately after the completion of paclitaxel administration, carboplatin was mixed with 250 mL of physiological saline or 5% glucose solution, and the mixture was administered over one hour. This administration was conducted for 3 or more courses, up to 6 courses.

RECIST criteria (revised version of the WHO criteria published in the WHO Handbook for reporting results of cancer treatment) was used for evaluating tumor-shrinking effects. In this protocol, the appearance of new lesions of bone metastases was evaluated as PD. Tumor markers were not used for evaluating non-target lesions.

Evaluation of Target Lesions

1) Complete Response: CR

Disappearance of all target lesions including secondary changes due to tumor

2) Partial Response: PR

At least a 30% decrease in the sum of the longest diameter of target lesions as compared to that before treatment 3) Stable Disease: SD Neither shrinkage of tumor to qualify for CR or PR nor increase in tumor to qualify for PD over 6 or more weeks 4) Progressive Disease: PD
At least a 20% increase in the sum of the longest diameter of target lesions (including recurrence), taking as reference the smallest sum (including a baseline value) of the longest diameter of target lesions that was previously observed Evaluation of Non-target Lesions
1) Complete Response: CR
Disappearance of all non-target lesions
2) Incomplete Response: IR, Stable Disease: SD
Persistence of non-target lesions
3) Progressive Disease: PD
Unequivocal increase in non-target lesions (including recurrence)

Overall Evaluation of Effectiveness

TABLE 1

| Overall response | Target lesions | Non-target lesions | Appearance of new lesions |
|---|---|---|---|
| CR | CR | CR | No |
| PR | CR | IR/SD | No |
|  | PR | Non-PD | No |
| SD | SD | Non-PD | No |
| PD | PD | Any | Yes or No |
|  | Any | PD | Yes or No |
|  | Any | Any | Yes |

Response rate was defined as the proportion of patients whose best overall response was either CR or PR according to the above-described RECIST criteria, among eligible patients having measurable lesions.

Progression-free survival was defined as the period from the date of registration to the date when disease progression was observed or the date of death from any cause, whichever came first. In the case where neither event was observed, the observation was stopped at the latest assessment.

The protein expression level of thymidylate synthase in tumor tissues was semiquantified by immunohistochemical staining using formalin-fixed paraffin-embedded sections of tumor tissues of surgical or biopsy specimens. An anti-human thymidylate synthase rabbit polyclonal antibody that is specifically reactive with human thymidylate synthase was used as a primary antibody (Gan To Kagaku Ryoho. 1997; 24(6): 705-12). H-score, which is determined using the following calculation formula, was adopted as a method of assessing the protein expression level. Cytoplasm, a major localization of thymidylate synthase, was assessed.

H-score=$\Sigma$ (staining intensity×percentage of positive cells (%))

(staining intensity 0: unstained,
staining intensity 1: weak staining,
staining intensity 2: moderate staining,
staining intensity 3: strong staining)

In order to predict what cases can obtain CR or PR as the best overall response of TS-1/carboplatin combination group, an optimal cut-off point, in which the sum of sensitivity and specificity was maximal, was calculated using the determined H-score according to ROC analysis. The calculated optimal cut-off point was 45.

Further, cut-off points that ensure a significant proportion to obtain CR or PR as the best overall response of TS-1/carboplatin combination group according to the chi-square test were calculated using the determined H-score. The calculated cut-off points were 30 to 70. Among these values, the cut-off points in which the P-value of the log-rank test was 0.05 or less was 30 to 45. The calculated cut-off points (30, 45, and 70) were used to divide the patients into two groups, i.e., low expression and high expression groups of thymidylate synthase (TS); and survival analysis was conducted. The results are shown in Tables 2 to 4.

TABLE 2

Cut-off point: 30

| Subject | The number of cases | Response rate (%) | Median progression-free survival (month) |
|---|---|---|---|
| TS-1/carboplatin combination group Low expression level of TS | 4 | 100.0 | 7.0 |
| TS-1/carboplatin combination group High expression level of TS | 18 | 27.8 | 2.4 |

TABLE 3

Cut-off point: 45

| Subject | The number of cases | Response rate (%) | Median progression-free survival (month) |
|---|---|---|---|
| TS-1/carboplatin combination group Low expression level of TS | 6 | 100.0 | 5.8 |
| TS-1/carboplatin combination group High expression level of TS | 16 | 18.8 | 2.0 |

TABLE 4

Cut-off point: 70

| Subject | The number of cases | Response rate (%) | Median progression-free survival (month) |
|---|---|---|---|
| TS-1/carboplatin combination group Low expression level of TS | 11 | 63.6 | 5.8 |
| TS-1/carboplatin combination group High expression level of TS | 11 | 18.2 | 3.3 |

As a result, the patients with low expression levels of thymidylate synthase in tumor tissues had a response rate of 63.6 to 100%, and median progression-free survival of 5.8 to 7.0 months. As compared to the case where patients are not stratified by the expression level of thymidylate synthase (response rate: 40.9%, and median progression-free survival: 3.3 months), remarkably high therapeutic effects were obtained with about 20 to 60% increase in response rate, and about 2.5- to 3.7-month prolongation of median progression-free survival. Further, for these patients with low expression levels of thymidylate synthase, significantly excellent therapeutic effects were obtained with remarkably improved response rate and progression-free survival, even as compared to paclitaxel/carboplatin combination therapy (response rate: 37.5%, and median progression-free survival: 3.3 months), which hitherto provided the most excellent effect among existing combination therapies using chemotherapeutics.

The above results show that the therapeutic effect of TS-1/carboplatin is remarkably increased by selecting non-small-cell lung cancer patients according to the index, i.e., the level of thymidylate synthase.

The invention claimed is:

1. A therapeutic method of treating non-small-cell lung cancer, in a patient, comprising
   (1) measuring an expression level of thymidylate synthase gene in a biological sample obtained from a patient, wherein said biological sample is believed to contain cancer cells; and
   (2) predicting that the patient will respond to a combination chemotherapy with carboplatin and a combination drug of tegafur/gimeracil/oteracil potassium when the expression level of thymidylate synthase gene measured in step (1) is lower than a predetermined cut-off point, and
   (3) administering the combination chemotherapy to the patient after predicting that the patient will respond to the combination chemotherapy.

2. The method according to claim 1, wherein the predetermined cut-off point is a value selected from the following:
   [1] an average or median value of the expression level of thymidylate synthase gene in patients who have undergone combination chemotherapy with carboplatin and a combination drug of tegafur/gimeracil/oteracil potassium;
   [2] a value determined based on ROC (Receiver Operating Characteristic) analysis such that the sum of sensitivity and specificity becomes maximal from the relevance between the expression level of thymidylate synthase gene in patients who have undergone combination chemotherapy with carboplatin and a combination drug of tegafur/gimeracil/oteracil potassium, and with or without a therapeutic effect of the combination chemotherapy; and
   [3] a value determined based on the chi-square test from the relevance between the expression level of thymidylate synthase gene in patients who have undergone combination chemotherapy with carboplatin and a combination drug of tegafur/gimeracil/oteracil potassium, and a therapeutic effect of the combination chemotherapy.

3. The method according to claim 2, wherein the predetermined cut-off point is a value determined based on the chi-square test and is a value determined such that the P-value of the log-rank test is 0.05 or less.

4. The method according to claim 1, wherein the predetermined cut-off point is 30 to 70 calculated by the H-score method.

5. The method according to claim 1, wherein the predetermined cut-off point is 45 calculated by the H-score method.

* * * * *

UNITED STATES PATENT AND TRADEMARK OFFICE
CERTIFICATE OF CORRECTION

PATENT NO. : 8,598,188 B2
APPLICATION NO. : 13/255550
DATED : December 3, 2013
INVENTOR(S) : Nakagawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 13 days.

Signed and Sealed this
Twenty-second Day of September, 2015

Michelle K. Lee
*Director of the United States Patent and Trademark Office*